United States Patent
Wismer

[11] Patent Number: 5,608,124
[45] Date of Patent: Mar. 4, 1997

[54] PROCESS FOR CONTINUOUS LIQUID PHASE REACTION OF HYDROGEN FLUORIDE AND 1,1,1-TRICHLOROETHANE TO PROVIDE 1,1-DICHLORO-1-FLUOROETHANE AND 1-CHLORO-1, 1-DIFLUOROETHANE MIXTURES

[75] Inventor: John A. Wismer, Devon, Pa.

[73] Assignee: Elf Atochem North America, Inc., Philadelphia, Pa.

[21] Appl. No.: 879,068

[22] Filed: May 1, 1992

Related U.S. Application Data

[63] Continuation of Ser. No. 561,212, Jul. 30, 1990, abandoned, which is a continuation of Ser. No. 365,345, Jun. 13, 1989, abandoned.

[51] Int. Cl.$^6$ ............................................. C07C 17/20
[52] U.S. Cl. ....................................................... 570/164
[58] Field of Search ............................................. 570/164

[56] References Cited

U.S. PATENT DOCUMENTS 2,058,453 10/1936 Holt et al. .
2,450,414 10/1948 Benning .
3,833,676 9/1974 Ukaji et al. .

OTHER PUBLICATIONS

Chem. Abstracts 85:123323v (1976).

Primary Examiner—Alan Siegel
Attorney, Agent, or Firm—Seidel, Gonda, Lavorgna & Monaco, P.C.

[57] ABSTRACT

A continuous non-catalytic process for the manufacture of 1,1-dichloro-1-fluoroethane/1-chloro-1,1-difluoroethane mixtures from 1,1-dichloro-1-fluoroethane is provided. Hydrogen fluoride and 1,1,1-trichloroethane are continuously feed a molar ratio of from about 3.0 to about 5.2 to form a liquid phase hydrofluorination reaction mixture. Vapor phase reaction product is continuously withdrawn from the reaction zone, and hydrogen fluoride is continuously selectively refluxed back to the reaction mixture. 1,1,1-Trichloroethane utilization approaches 100%, with selectivity for 1,1-dichloro-1-fluoroethane between 15% and 85%, based upon the amount of 1,1-dichloro-1-fluoroethane and 1-chloro-1,1-difluoroethane contained in the gaseous reaction product.

6 Claims, 1 Drawing Sheet

5,608,124

PROCESS FOR CONTINUOUS LIQUID PHASE REACTION OF HYDROGEN FLUORIDE AND 1,1,1-TRICHLOROETHANE TO PROVIDE 1,1-DICHLORO-1-FLUOROETHANE AND 1-CHLORO-1, 1-DIFLUOROETHANE MIXTURES

This is a continuation of application Ser. No. 07/561,212 filed on Jul. 30, 1990 now abandoned which is a continuation of application Ser. No. 365,345 filed on Jun. 13, 1989 now abandoned.

FIELD OF THE INVENTION

The invention relates generally to the production of 1,1-dichloro-1-fluoroethane and 1-chloro-1,1-difluoroethane, more particularly to a process for the production of 1,1-dichloro-1-fluoroethane and 1-chloro-1,1-difluoroethane by the fluorination of 1,1,1-trichloroethane with hydrogen fluoride.

BACKGROUND OF THE INVENTION 1,1-Dichloro-1-fluoroethane and 1-chloro-1,1-difluoroethane may be produced by the liquid phase hydrofluorination of 1,1,1-trichloroethane. The reactor effluent contains, principally, these hydrochlorofluorocarbons and any hydrogen fluoride in excess of the stoichiometric amount required for complete reaction of 1,1,1-trichloroethane. While a variety of catalysts have been proposed for catalyzing the reaction, the system is sufficiently reactive to render a catalyst unnecessary.

U.S. Pat. No. 3,833,676 describes a non-catalytic batch process for fluorinating 1,1,1-trichloroethane with hydrogen fluoride. High hydrogen fluoride/1,1,1-trichloroethane ratios are recommended for maximizing conversion of 1,1,1-trichloroethane.

The process of U.S. Pat. No. 3,833,676 suffers from several disadvantages. Productivity is limited by the batchwise nature of the production scheme disclosed in said patent. A large excess of hydrogen fluoride remains in the reaction product. While U.S. Pat. No. 3,833,676 prefers a molar ratio of hydrogen fluoride to 1,1,1-trichloroethane in the range of between about from 4 to 30, reaction rate is slow, implying that high selectivity for 1,1-dichloro-1-fluoroethane is impossible, at the lower ratios. Presumably, phase separation occurs at lower HF/1,1,1-trichloroethane molar ratios when the reaction is operated in batchwise fashion as disclosed in U. S. Pat. No. 3,833,676.

Various patents describe processes in which reactants are introduced into a reactive liquid phase, and products are withdrawn as gases. See, e.g. U.S. Pat. Nos. 2,450,414 and 2,058,453. However, such systems have not been heretofore applied to the reaction of 1,1,1-trichloroethane and hydrogen fluoride, to produce 1,1-dichloro-1-fluoroethane, or mixtures of 1,1-dichloro-1-fluoroethane and 1-chloro-1,1-difluoroethane.

SUMMARY OF THE INVENTION

A continuous non-catalytic process for the manufacture of a mixture of 1,1-dichloro-1-fluoroethane and 1-chloro-1,1-difluoroethane from 1,1,1-trichloroethane is provided. Hydrogen fluoride and 1,1,1-trichloroethane in a selected molar feed ratio are continuously fed to a reaction zone to form a liquid phase hydrofluorination reaction mixture in the reaction zone. Vapor phase reaction products are continuously withdrawn from the reaction zone, and hydrogen fluoride is continuously refluxed from the vapor phase reaction product to the hydrofluorination reaction mixture. A mixture of 1,1-dichloro-1-fluoroethane and 1-chloro-1,1-difluoroethane is obtained from the vapor phase reaction product.

The selected hydrogen fluoride/1,1,1-trichloroethane molar feed ratio (i) is within the range of from about 3.0 to about 5.2; and (ii) is greater than the value M determined by the equation $$M = 2.7X + 4.2Y$$

wherein

X is the desired mole fraction of 1-chloro-1,1-difluoroethane in the resulting 1,1-dichloro-1-fluoroethane/1-chloro-1,1-difluoroethane mixture; and Y is the desired mole fraction of 1,1-dichloro-1-fluoroethane in the resulting 1,1-dichloro-1-fluoroethane/1-chloro-1,1-difluoroethane mixture.

Preferably, the ratio of vapor removed as the reaction product, to vapor refluxed back to the reaction mixture, is about 1:1, by weight.

DESCRIPTION OF THE FIGURE

The FIG. 1 is a schematic illustration of an embodiment of the process of the invention.

DETAILED DESCRIPTION OF THE INVENTION

Figure 1:
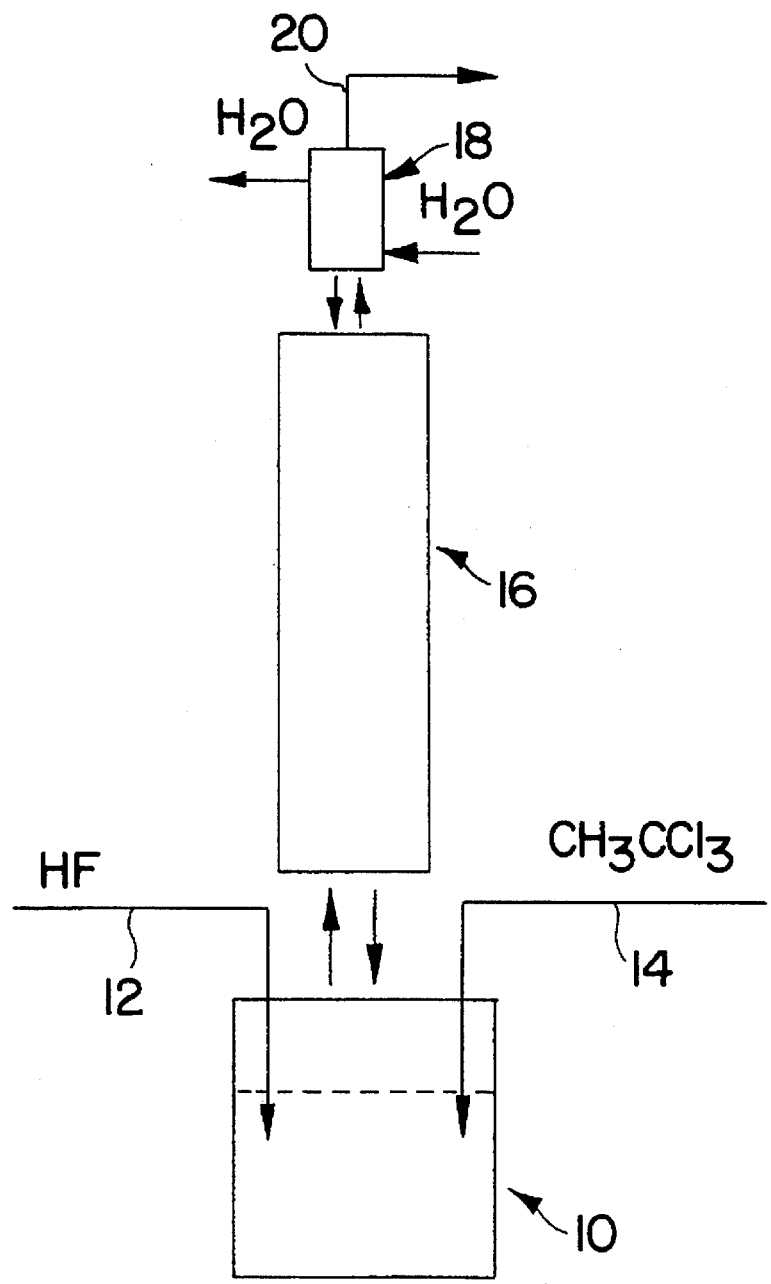

According to the process of the invention, hydrogen fluoride and 1,1,1-trichloroethane are reacted in a vessel under conditions which permits a liquid phase reaction to take place, but also permits removal of reaction product in the gaseous state. The gaseous product is partially rectified, such as in a distillation column, which permits the selective condensation of hydrogen fluoride and its reflux back to the reaction vessel. By removing the reaction product from the reaction vessel as a gas, the product contains much less hydrogen fluoride than if the product were removed as a liquid. Under steady state reaction conditions, the proportion of hydrogen fluoride in the liquid reaction phase is much higher than the proportion of hydrogen fluoride in the reaction product gas. By refluxing a portion of the vapor product back to the liquid phase reaction mixture, the process of the invention ensures that the liquid will contain a large molar excess of hydrogen fluoride relative to 1,1,1-trichloroethane. Excess hydrogen fluoride is required to maintain a single reaction phase, since 1,1,1-trichloroethane has low solubility in hydrogen fluoride. A large molar excess of hydrogen fluoride relative to 1,1,1-trichloroethane prevents the precipitation of 1,1,1-trichloroethane from the reaction mixture, and the resulting decrease in conversion of 1,1,1-trichloroethane to hydrofluorination product.

While the effect of the low solubility of 1,1,1-trichloroethane in hydrogen fluoride may be partially compensated by agitation, it is generally preferred that agitation is avoided in systems containing hydrogen fluoride, due to the acid's extreme corrosive effect on agitation mechanisms. The present invention therefore provides for the maintenance of a high conversion of 1,1,1-trichloroethane, even in the absence of agitation. Agitation is unnecessary since a large molar excess of hydrogen fluoride to 1,1,1-trichloroethane is continuously contained in the liquid phase reaction mixture, thereby minimizing the precipitation of 1,1,1-trichloroethane and the formation of reactor "tars".

The invention provides for the continuous steady state production of 1,1-dichloro-1-fluoroethane/1-chloro-1,1-difluoroethane mixtures at the minimum hydrogen fluor-ide/1, 1,1-trichloroethane molar feed ratio required by the hydrofluorination reaction stoichiometry and thermodynamics. By maintaining the hydrogen fluoride feed to the reaction vessel at a minimum, and selectively refluxing hydrogen fluoride from the vapor phase product back to the liquid phase reaction mixture, the cost of a separation train to remove hydrogen fluoride from the reaction product is minimized. At the same time however, the process of the invention provides for selectivities for 1,1-dichloro-1-fluoroethane as low as 15% and as high as 85%, with 98–100% conversion of 1,1,1-trichloroethane, at the relatively low HF:1,1,1-trichloroethane molar feed ratios of from about 3.0 to about 5.2.

Preferably, the process is utilized to obtain mixtures of 1,1-dichloro-1-fluoroethane and 1-chloro-1,1-difluoroethane comprising from about 50 wt. % to about 85 wt. % 1,1-dichloro-1-fluoroethane, most preferably, about 75 wt. % to about 85 wt. %.

The process of the invention is illustrated in FIG. 1. A reaction zone for the liquid phase reaction of hydrogen fluoride and 1,1,1-trichloroethane is defined by a reactor vessel 10. The vapor phase product is collected in line 20. The vessel may have the typical construction known to those skilled in the art for the continuous hydrofluorination of halocarbons. The reactor is first filled with hydrogen fluoride before initiating the continuous feed of hydrogen fluoride and 1,1,1-trichloroethane from lines 12 and 14, respectively.

The reactor vessel 10 is preferably of the jacketed type. Steam is delivered to the reactor jacket in such a way as to preferably maintain the pressure inside the reaction vessel at a constant level.

Vapor phase reaction product, comprising 1,1-dichloro-1-fluoroethane, 1-chloro-1,1-difluoroethane, hydrogen chloride and hydrogen fluoride, and possibly minor amounts of nonselective reaction products, is continuously withdrawn from reactor vessel 10 into distillation column 16. For an 80/20 1,1-dichloro-1-fluoroethane/1-chloro-1,1-difluoroethane mole ratio, for example, distillation column 16 is operated, for example, at a column top temperature of about 150° F. and a column bottom temperature of about 180° F. and a pressure of about 115 PSIG. A reflux condensor 18 selectively condenses hydrogen fluoride and refluxes liquid hydrogen fluoride back through column 16 to the reactor vessel 10. The vapor phase product is collected in line 20. The reflux conditions are preferably adjusted such that about 1 part of vapor is refluxed, for every part of vapor taken overhead, by weight. Vapor is taken overhead at a constant rate which is approximately equal to the sum of the rates of the hydrogen fluoride and 1,1,1-trichloroethane reactant feeds in lines 12 and 14. The hydrochlorofluorocarbon concentration is greatest at the top of the column, and lowest in reactor vessel 10. This concentration gradient allows the hydrogen fluoride concentration in the reactor vessel to be at all times large enough to insure substantially complete solvation of 1,1,1-trichloroethane. Consequently, the 1,1,1-trichloroethane conversion approaches 100%. The amount of unreacted 1,1,1-trichloroethane left in the reaction vessel is very low, typically less than 2% of the reactor feed, by weight. Any 1,1,1-trichloroethane which precipitates from the reaction phase may be periodically withdrawn from the reactor bottom. Since the present invention maximizes the conversion of 1,1,1-trichloroethane, the formation of precipitated 1,1,1-trichloroethane, and the need to periodically withdraw the same from the reactor bottom, is kept to a minimum.

The minimum molar feed ratio required to attain a targeted 1,1-dichloro-1-fluoroethane/1-chloro-1,1-difluoroethane reaction product ratio is dictated by Equation 1, $$M = 2.7X + 4.2Y \qquad \text{(Equation 1)}$$

wherein,

X is the desired mole fraction of 1-chloro-1,1-difluoroethane obtained as product, with respect to the total amount of 1,1-dichloro-1-fluoroethane and 1-chloro-1,1-difluoroethane produced; and Y is the desired mole fraction of 1,1-dichloro-1-fluoroethane obtained as product, with respect to the total amount of 1,1-dichloro-1-fluoroethane and 1-chloro-1,1-difluoroethane produced.

The molar feed ratio dictated by Equation 1 takes into account the stoichiometry of the hydrofluorination reaction and the vapor/liquid equilibrium ("VLE") of the reaction components.

In the case of a process targeted to produce 1,1-dichloro-1-fluoroethane and 1-chloro-1,1-difluoroethane in a mole ratio of 80/20, Equation 1 dictates that the molar feed ratio of hydrogen fluoride to 1,1,1-trichloroethane should be set at a value of at least about 4.5.

Maintaining the HF:1,1,1-trichloroethane molar feed ratio above the minimum value defined by Equation 1 for a given targeted 1,1-dichloro-1-fluoroethane/1-chloro-1,1-difluoroethane product distribution ensures steady state reaction behavior, and substantially complete conversion of 1,1,1-trichloroethane. Below the theoretical minimum predicted by Equation 1, substantially less than complete conversion 1,1,1-trichloroethane is achieved, indicating unsteady state reaction behavior.

In practice, the reflux of excess hydrogen fluoride may be incomplete, i.e., some hydrogen fluoride in excess of that required by the vapor/liquid equilibrium may escape reflux back to the reaction zone, and may be carried overhead with the vapor phase reaction products. Thus, it is desirable to utilize a HF:1,1,1-trichloroethane molar feed ratio slightly higher than the minimum value required by Equation 1. This is accomplished by introducing a "safety factor" S into Equation 1, to take into account possible incomplete rectification. The equation thus becomes, $$M = (2.7X + 4.2Y)S \qquad \text{(Equation 2)}$$

wherein,

X and Y are defined as above; and

S is a number selected from 1.01 to 1.30.

According to Equation 2, 1,1-dichloro-1-fluoroethane and 1-chloro-1,1-difluoroethane may be produced in ratios of from about 85:15 mol % to 15:85 mol %, by utilizing HF/1,1,1-trifluoroethane molar feed ratios in the range of from about 3.0 to about 5.2.

The process of the invention results in a product mixture comprising 1,1-dichloro-1-fluoroethane and 1-chloro-1,1-difluoroethane, which contains only minor amounts of the fully fluorinated product 1,1,1-trifluoroethane, typically, no more than about 0.5 wt. %, based upon the weight of the product gas taken overhead.

Once the HF:1,1,1-trichloroethane molar feed ratio is fixed at or above the minimum ratio required by Equation 1 (or, alternatively, by Equation 2) for a given targeted 1,1- dichloro-1-fluoroethane/1-chloro-1,1-difluoroethane product distribution, the relative amounts of 1,1-dichloro-1-fluoroethane and 1-chloro-1,1-difluoroethane obtained in the overhead product gas may be varied from the targeted amounts by manipulating the reflux ratio, reactor pressure and/or reactant residence time. Increasing the reactor pressure or reactant residence time generally favors the formation of 1-chloro-1,1-difluoroethane over 1,1-dichloro-1-fluoroethane.

When 1,1-dichloro-1-fluoroethane is desired as the predominant product, the reflux ratio is necessarily a compromise between two considerations. A higher reflux ratio results in the selective reflux of hydrogen fluoride with respect to hydrochlorofluorocarbon compounds taken overhead, but also results in the selective reflux of 1,1-dichloro-1-fluoroethane relative to 1-chloro-1,1-difluoroethane. Thus, increasing the reflux ratio results not only in the enrichment of HF in the reactor pot with respect to 1,1-dichloro-1-fluoroethane and 1-chloro-1,1-difluoroethane, but also results in the enrichment of 1,1-dichloro-1-fluoroethane relative to 1-chloro-1,1-difluoroethane. The refluxed 1,1-dichloro-1-fluoroethane reacts with hydrogen fluoride to produce additional 1-chloro-1,1-difluoroethane. Thus, production of the more fluorinated product 1-chloro-1,1-difluoroethane is favored at higher reflux ratios. A reflux ratio of about 1 pound reflux per pound of gas taken overhead from column 16 appears to be a reasonable balance between these two competing considerations. The reflux ratio is controlled by varying the temperature and/or rate of flow of cooling water through reflux condensor 18.

The vapor taken as a reflux top product generally comprises 1,1-dichloro-1-fluoroethane, 1-chloro-1,1-difluoroethane, hydrogen chloride and any hydrogen fluoride which is not refluxed back to the reactor vessel. It may also include unreacted 1,1,1-trichloroethane, and some nonselective reaction products such as 1,1,1-trifluoroethane, 1,1,1,3,3-pentafluorobutane and 1,1-dichloroethylene. The hydrogen chloride may be separated from the reaction product by distillation. The hydrogen fluoride and hydrochlorofluorocarbons may be separated by a combination of phase separation and distillation in such a way to return the excess hydrogen fluoride to the reactor as a recycle. In the event that hydrogen fluoride is recycled to the hydrofluorination zone, the molar ratio of hydrogen fluoride to 1,1,1-trichloroethane prescribed by Equations 1 and 2 is based upon the total amount of hydrogen fluoride fed to the reactor, including both the hydrogen fluoride supplied as a feed in line 12 and any recycle hydrogen fluoride supplied to the reactor from the downstream separation of hydrogen fluoride from the hydrochlorofluorocarbon reaction products.

The process of the invention provides for the hydrofluorination of 1,1,1-trichloroethane to 1,1-dichloro-1-fluoroethane and 1-chloro-1,1-difluoroethane mixtures in such a manner so as to maximize 1,1,1-trichloroethane conversion and minimize hydrogen fluoride carried in the overhead reaction product gas. In an uncatalyzed system, the amount of hydrogen fluoride carried over into the product stream is a function of the vapor/liquid equilibrium. For the production of 1-chloro-1,1-difluoroethane, the minimum theoretical molar feed ratio of hydrogen fluoride to 1,1,1-trichloroethane is about 2.7 in order to simultaneously satisfy reaction stoichiometry and vapor/liquid equilibrium requirements. Of this amount, 2 moles of hydrogen fluoride react with 1,1,1-trichloroethane to form 1-chloro-1,1-difluoroethane and 0.7 moles of hydrogen fluoride are carried overhead for each mole of 1-chloro-1,1-difluoroethane produced. This is because an azeotrope of about 40 mol % hydrogen fluoride forms with 1-chloro-1,1-difluoroethane.

I have found, quite unexpectedly, that it is necessary to increase, rather than decrease, the HF:1,1,1-trichloroethane molar feed ratio in order to increase the ratio of 1,1-dichloro-1-fluoroethane to 1-chloro-1,1-difluoroethane in the product mixture. This is unexpected because, from the viewpoint of reaction stoichiometry, 50% less hydrogen fluoride should be required to form 1,1-dichloro-1-fluoroethane than 1-chloro-1,1-difluoroethane. Moreover, since 1,1-dichloro-1-fluoroethane is less volatile than hydrogen fluoride, it would be expected that rectification of the vapor phase product according to the present invention would be impossible. However, I have found that this is not the case. In fact, the hydrogen fluoride/1,1-dichloro-1-fluoroethane system is so non-ideal that, substantial rectification is possible. Moreover, I have found that, quite unexpectedly, the molar ratio of hydrogen fluoride to 1,1,1-trichloroethane in the reactor feed must be increased, rather than decreased, to maintain the steady state production of 1,1-dichloro-1-fluoroethane-rich mixtures of 1,1-dichloro-1-fluoroethane and 1-chloro-1,1-difluoroethane.

If insufficient hydrogen fluoride is supplied to the reaction zone, unsteady state behavior results therein. The unsteady state behavior is caused by underutilization of 1,1,1-trichloroethane, which accumulates as a second phase in the reactor bottom. Assuming constant reactor volume, the accumulation of 1,1,1-trichloroethane effectively results in a decrease of reactive phase residence time in the reaction zone, causing the 1,1-dichloro-1-fluoroethane/1,1,1-trichloroethane product ratio to shift from the targeted ratio. On the other hand, if too much hydrogen fluoride is supplied to the reaction zone, inefficiencies in downstream separation of hydrogen fluoride from the hydrochlorofluorocarbon product stream results.

The practice of the invention is illustrated in more detail in the following non-limiting examples.

EXAMPLE 1

Hydrogen fluoride and 1,1,1-trichloroethane were continuously fed into a ten gallon reactor coupled to a 3 inch by 15 foot rectification column. The molar feed ratio was held at 3.9:1 hydrogen fluoride to 1,1,1-trichloroethane, or slightly below the theoretical minimum of 4.0 predicted by Equation 1 for obtaining a product comprising 80 parts 1,1-dichloro-1-fluoroethane and 20 parts 1-chloro-1,1-difluoroethane, by mole. The pressure in the system was 115 PSIG and the rectifier was operated at a nominal reflux ratio of 0.62 pounds of gas refluxed, per pound of gas taken overhead. The calculated 1,1,1-trichloroethane utilization from the reaction was 98% indicating non-steady state behavior. The major components in the overhead product gas, following an average reactant residence time of 3.5 hours, were as follows:

|  | Wt % |
|---|---|
| HF | 27.2 |
| HCl | 20.3 |
| 1,1-dichloro-1-fluoroethane | 43.3 |
| 1-chloro-1,1-difluoroethane | 9.1 |
| 1,1,1-trifluoroethane | 0.1 |
|  | 100% |

EXAMPLE 2

The procedure of Example 1 was followed except the average reactant residence time in the reactor was lowered slightly to 3.35 hours, and the reflux ratio was increased to 0.98. The hydrogen fluoride/1,1,1-trichloroethane molar feed ratio was increased to the theoretical minimum of 4.0 required by Equation 1. The calculated 1,1,1-trichloroethane utilization increased to 100%. The composition of the overhead gas was as follows:

|  | Wt % |
| --- | --- |
| HF | 25.8 |
| HCl | 20.6 |
| 1,1-dichloro-1-fluoroethane | 44.3 |
| 1-chloro-1,1-difluoroethane | 9.2 |
| 1,1,1-trifluoroethane | 0.1 |
|  | 100% |

EXAMPLE 3

The procedure of Example 1 was followed utilizing a hydrogen fluoride/1,1,1-trichloroethane molar feed ratio of 2.9 to obtain a 1,1-dichloro-1-fluoroethane/1-chloro-1,1-difluoroethane product ratio of 57.5/42.5. The nominal reflux ratio was 0.92 pounds reflux per pound of material carried overhead. The system pressure was 160 PSIG, with an average reactant residence time of 4.5 hours. The calculated 1,1,1-trichloroethane conversion was only 92%, indicating unsteady state behavior. The overhead gas composition was as follows:

|  | Wt % |
| --- | --- |
| HF | 22.4 |
| HCl | 25.1 |
| 1,1-dichloro-1-fluoroethane | 31.9 |
| 1-chloro-1,1-difluoroethane | 20.3 |
| 1,1,1-trifluoroethane | 0.3 |
|  | 100% |

Equation 1 predicts that a minimum molar feed ratio of hydrogen fluoride to 1,1,1-trichloroethane of 3.6 is required to maintain a 1,1-dichloro-1-fluoroethane/1-chloro-1,1-difluoroethane mole product ratio of 57.5/42.5. With only 2.9 moles or hydrogen fluoride to 1,1,1-trichloroethane in the reactor feed, substantially unsteady state behavior resulted, as evidenced by conversion of only 92% 1,1,1-trichloroethane in Example 3.

EXAMPLE 4

The procedure of Example 3 was repeated except that the average residence time was increased to 5.2 hours, and the nominal reflux ratio was decreased to 0.8 pounds of gas refluxed per pound of gas carried overhead. A molar feed ratio of 3.5 HF:1,1,1-trichloroethane was utilized, resulting in steady state system behavior, with a calculated 1,1,1-trichloroethane utilization of 98.2%. The overhead gas composition was as follows:

|  | Wt % |
| --- | --- |
| HF | 19.7 |
| HCl | 28.9 |
| 1,1-dichloro-1-fluoroethane | 21.1 |
| 1-chloro-1,1-difluoroethane | 29.5 |
| 1,1,1-trifluoroethane | 0.5 |
|  | 100% |

The present invention may be embodied in other specific forms without departing from the spirit or essential attributes thereof and, accordingly, reference should be made to the appended claims, rather than to the foregoing specifications, as indicating the scope of the invention.

I claim:

1. A continuous non-catalytic process for the manufacture of a mixture of 1,1-dichloro-1-fluoroethane and 1-chloro-1,1-difluoroethane from 1,1,1-trichloroethane comprising:

(a) continuously feeding hydrogen fluoride and 1,1,1-trichloroethane in a selected molar feed ratio to a reaction zone containing HF to form a liquid phase hydrofluorination reaction mixture in said reaction zone which reaction mixture contains a large molar excess of HF relative to 1,1,1-trichloroethane;

(b) continuously withdrawing from the reaction zone, vapor phase reaction product comprising 1,1-dichloro-1-fluoroethane and 1-chloro-1,1-difluoroethane;

(c) continuously refluxing hydrogen fluoride from the vapor phase reaction product to the reaction mixture to maintain a large molar excess of HF relative to 1,1,1-trichloroethane in the reaction mixture sufficient to prevent substantial precipitation of 1,1,1-trichloroethane from the reaction mixture"has been added after mixture"; and (d) obtaining a mixture of 1,1-dichloro-1-fluoroethane and 1-chloro-1,1-difluoroethane from the vapor phase reaction product;

wherein said selected hydrogen fluoride/1,1,1-trichloroethane molar feed ratio (i) is within the range of from about 3.0 to about 5.2; and (ii) is greater than the value M determined by the equation $$M = 2.7X + 4.2Y$$

wherein

X is the desired mole fraction of 1-chloro-1,1-difluoroethane in the resulting 1,1-dichloro-1-fluoroethane/1-chloro-1,1-difluoroethane mixture; and Y is the desired mole fraction of 1,1-dichloro-1-fluoroethane in the resulting 1,1-dichloro-1-fluoroethane-/1-chloro-1,1-difluoroethane mixture.

2. A process according to claim 1 wherein the reflux ratio is about 1:1, by weight.

3. A process according to claim 1 wherein the vapor phase reaction product is withdrawn at a constant rate equal to the sum of the rates at which hydrogen fluoride and 1,1,1-trichloroethane are fed into the reaction zone.

4. A process according to claim 1 wherein the vapor phase reaction product contains no more than about 0.5 wt. % 1,1,1-trifluoroethane.

5. A process according to claim 1 wherein the mixture of 1,1-dichloro-1-fluoroethane and 1-chloro-1,1-difluoroethane obtained comprises from about 50 wt. % to about 85 wt. % 1,1-dichloro-1-fluoroethane.

6. A process according to claim 5 wherein the mixture comprises from about 75 wt. % to about 85 wt. % 1,1-dichloro-1-fluoroethane.

* * * * *